United States Patent
Coates et al.

(10) Patent No.: US 9,482,218 B2
(45) Date of Patent: Nov. 1, 2016

(54) DEFORMABLE MEMBRANE PUMP FOR DIALYSIS MACHINE

(75) Inventors: James Coates, Droitwich (GB); Mark Wallace, Kinver (GB); Clive Buckberry, Warwick (GB)

(73) Assignee: Quanta Fluid Solutions Ltd., Warwickshire (GB)

( * ) Notice: Subject to any disclaimer, the term of this patent is extended or adjusted under 35 U.S.C. 154(b) by 648 days.

(21) Appl. No.: 13/394,166

(22) PCT Filed: Sep. 3, 2010

(86) PCT No.: PCT/GB2010/001667
§ 371 (c)(1),
(2), (4) Date: Jul. 16, 2012

(87) PCT Pub. No.: WO2011/027118
PCT Pub. Date: Mar. 10, 2011

(65) Prior Publication Data
US 2012/0275943 A1 Nov. 1, 2012

(30) Foreign Application Priority Data

Sep. 3, 2009 (GB) .................................. 0915327.1

(51) Int. Cl.
*F04B 43/06* (2006.01)
*A61M 1/10* (2006.01)
*A61M 1/14* (2006.01)

(52) U.S. Cl.
CPC .............. *F04B 43/06* (2013.01); *A61M 1/106* (2013.01); *A61M 1/1062* (2014.02); *A61M 1/14* (2013.01)

(58) Field of Classification Search
CPC ......... A61M 5/1422; A61M 5/14416; A61M 5/14224; A61M 5/14212; F04B 43/06; F04B 43/0054; F04B 43/04; F04B 43/043; F04B 43/046; F04B 43/067; F04B 45/04; F04B 45/057; F04B 45/053; F04B 45/0533; F04B 45/0536
USPC .................. 417/417, 394, 395, 413.1, 413.2; 604/29, 151, 152; 92/96
See application file for complete search history.

(56) References Cited

U.S. PATENT DOCUMENTS

| | | | | |
|---|---|---|---|---|
| 3,338,171 | A * | 8/1967 | Conklin | F01L 23/00 417/339 |
| 3,468,261 | A * | 9/1969 | Schmierer | F04B 43/02 417/567 |
| 3,606,592 | A * | 9/1971 | Madurski | A61M 1/1053 417/413.1 |
| 3,807,906 | A * | 4/1974 | Breit | F04B 43/0063 417/383 |
| 4,368,261 | A * | 1/1983 | Klose | C12Q 1/44 435/15 |
| 4,430,048 | A * | 2/1984 | Fritsch | F04B 43/067 417/383 |
| 4,494,912 | A * | 1/1985 | Pauliukonis | F04B 9/115 137/106 |
| 5,385,540 | A * | 1/1995 | Abbott | A61M 1/3664 128/DIG. 3 |

(Continued)

FOREIGN PATENT DOCUMENTS

| | | |
|---|---|---|
| EP | 0536818 | 4/1993 |
| WO | WO02/081917 | 10/2002 |

*Primary Examiner* — Devon Kramer
*Assistant Examiner* — Jon Hoffman
(74) *Attorney, Agent, or Firm* — Hahn Loeser & Parks, LLP

(57) ABSTRACT

A pump for a dialysis machine, the pump having a pump chamber and a deformable membrane actuable to pump a fluid from the pump chamber, the pump chamber being substantially conical such that the membrane is actuated to extend into the conical chamber in order to pump the fluid from the chamber.

4 Claims, 3 Drawing Sheets

(56) References Cited

U.S. PATENT DOCUMENTS

| | | | |
|---|---|---|---|
| 5,458,468 A | 10/1995 | Ye | |
| 5,476,368 A * | 12/1995 | Rabenau | F04B 53/101 417/395 |
| 5,957,670 A | 9/1999 | Duncan | |
| 6,582,206 B2 * | 6/2003 | Schluecker | F04B 43/0063 417/383 |
| 6,814,547 B2 * | 11/2004 | Childers | A61M 1/28 210/258 |
| 7,153,286 B2 * | 12/2006 | Busby | A61M 1/28 210/252 |
| 2003/0194332 A1 * | 10/2003 | Jahn | F04B 43/0733 417/395 |
| 2003/0217962 A1 * | 11/2003 | Childers | A61M 1/28 210/258 |
| 2004/0019313 A1 * | 1/2004 | Childers | A61M 1/284 604/5.01 |
| 2007/0278155 A1 * | 12/2007 | Lo | A61M 1/16 210/646 |
| 2009/0198174 A1 * | 8/2009 | Childers et al. | 604/29 |

\* cited by examiner

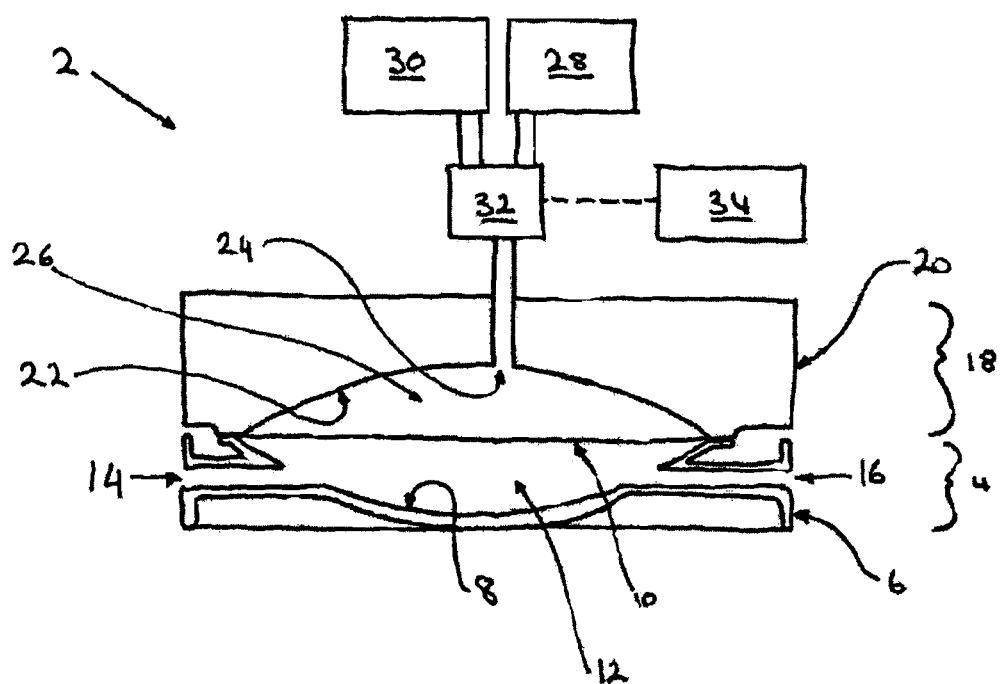
Figure 1 - PRIOR ART

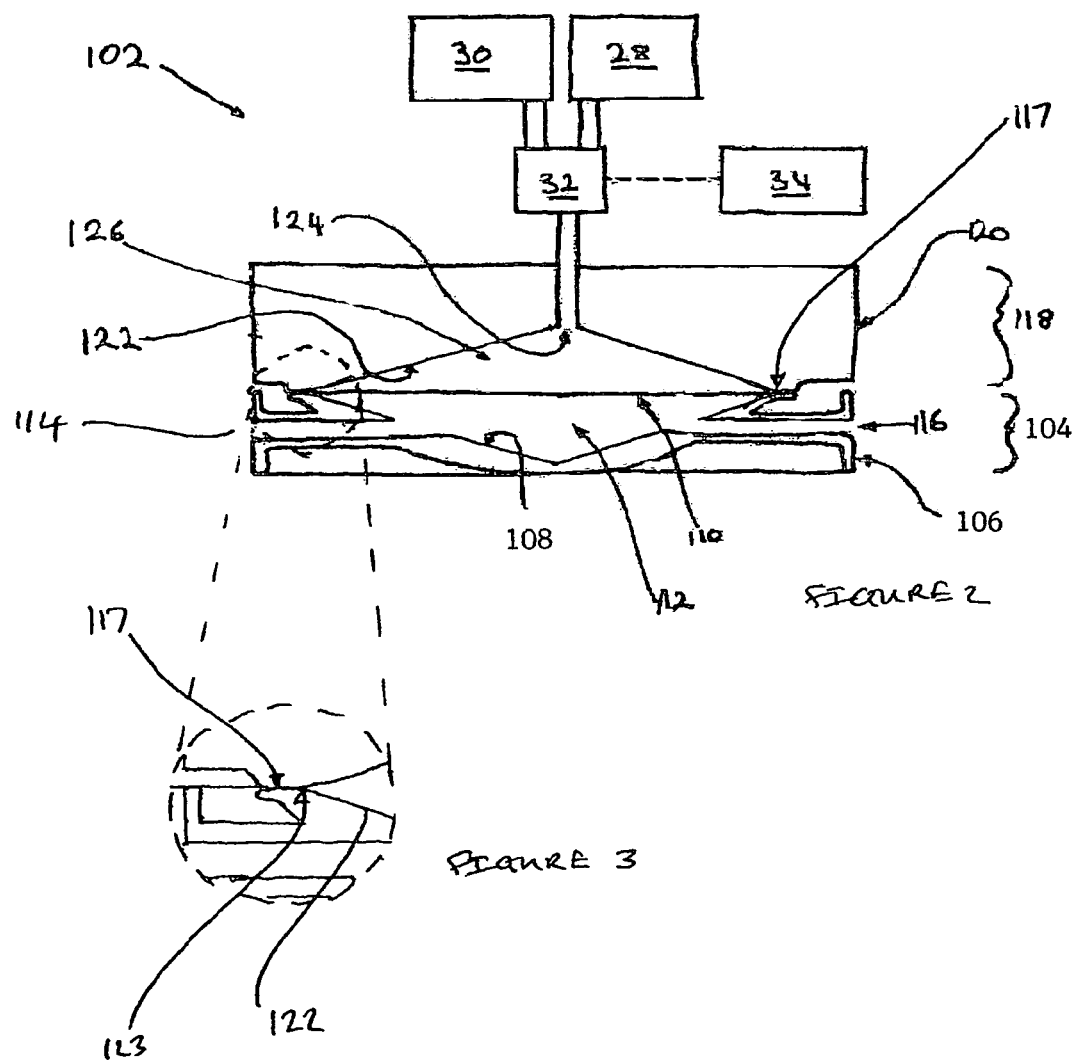

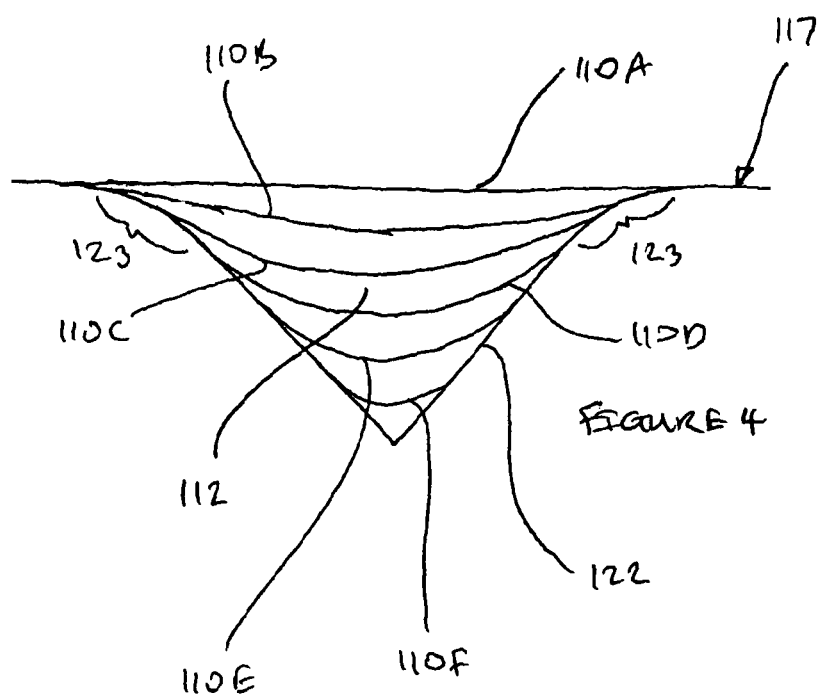

DEFORMABLE MEMBRANE PUMP FOR DIALYSIS MACHINE

CROSS-REFERENCE TO RELATED APPLICATIONS

This application claims priority from PCT/GB/2010/001667 filed on Sep. 3, 2010, and from GB 0915327.1 filed Sep. 3, 2009, all of which are hereby incorporated by reference in their entireties.

BACKGROUND OF THE INVENTION

1. Field of the Invention

The present invention relates to membrane pumps, and in particular, but not exclusively, to a membrane pump for a dialysis machine.

2. State of the Art

Membrane pumps are used in a number of medical applications, for example in hemodialysis for the extracorporeal circulation of blood and the preparation and delivery of dialysate to and from the dialyser. Commonly, the membrane covers a dome shaped pump chamber into which the membrane is actuated to draw fluid into, and pump the fluid from, the chamber.

A known pump is described with reference to FIG. 1 below. This form of pump has a number of drawbacks as follows.

The sharp angle between the concave recess of the drive chamber and the flat portion of the pump to which the membrane is attached causes high stresses in the membrane as it folds and stretches over the edge of the flat portion and into the recess upon actuation. This can lead to reduced life of the membrane.

Furthermore, the sharp angle between the flat portion and the recess can also cause the membrane to fold over the edge leaving a dead spot between the membrane and the recess wall where the membrane has not been actuated sufficiently to touch the chamber wall and expel fluid therebetween. This can lead to pumping inaccuracies and even to blood damage where the blood pools in this area for an unacceptable length of time.

The dome shaped profile of the pump chamber also presents a number of problems. The substantially hemispherical shape means that the membrane descends rapidly into the chamber upon actuation. Thus a large volume of fluid is pumped at the beginning of the stroke compared to the end of the stroke. Thus the volume of dispensed fluid can be difficult to control on the length of stroke. This can also lead to a hammer action of the pump which can lead to pumping inaccuracies and potential blood damage.

SUMMARY OF THE INVENTION

It is the purpose of the present invention to mitigate at least some of the above problems.

According to one aspect of the invention there is provided a pump for a dialysis machine, the pump having a pump chamber and a deformable membrane actuable to pump a fluid from the pump chamber, the pump chamber being substantially conical such that the membrane is actuated to extend into the conical chamber in order to pump the fluid from the chamber.

By providing a conical pump chamber the membrane descends into the chamber in a more controlled and predictable manner than the prior art pump. The displacement of fluid is more evenly distributes through the stroke of the membrane which improves the volumetric performance of the pump.

In a further aspect of the invention there is provided a pump for a dialysis machine, the pump having a pump chamber and an upper surface for supporting a deformable membrane actuable to pump a fluid, the pump chamber having an inner surface which extends downwardly from the upper surface, wherein arranged between the upper surface and the inner surface is a transition surface which has a curved profile so as to provide a smooth transition of the membrane within the pump chamber upon actuation of the pump.

The invention will now be described, by way of example only, and with reference to the following drawings.

BRIEF DESCRIPTION OF THE DRAWINGS

FIG. 1 is a representation of a prior art pump;

FIG. 2 is a representation of a pump according to the present invention;

FIG. 3 is a detailed representation part of the pump of FIG. 2; and

FIG. 4 is a representation of the deflection of the membrane within the chamber of the pump of FIG. 2.

DETAILED DESCRIPTION OF THE PREFERRED EMBODIMENTS

Referring to FIG. 1 a blood pump 2 is shown comprising a disposable pump cartridge 4 comprising a rigid plastic shell 6 having concave recess 8 covered by a flexible membrane 10. The recess 8 and the flexible membrane 10 form a pump cavity 12 having an inlet 14 and an outlet 16 leading into and out of the cavity respectively. The cartridge 4 abuts a pump driver 18 comprising a platen 20 having a recessed surface 22 therein and a fluid port 24. In use the platen 20 sealingly engages with the cartridge 4 such that the recessed surface 22 and the flexible membrane 10 form a drive chamber 26. The fluid port 24 is connectable with a source of positive fluid pressure 28 and a source of negative fluid pressure 30 via a valve 32, controlled by a controller 34 to allow fluid to flow into or out of the drive cavity 26. The positive 28 and negative 30 fluid sources are a pressure pump and a vacuum pump respectively. When the valve 32 is operated to allow fluid to flow into the drive chamber 26 from the source of positive fluid pressure 28, the membrane 10 is moved towards the recessed surface 8 and any blood that is in the pump cavity 12 is expelled via the outlet 16. When the valve 32 is operated to allow fluid to flow out of the drive chamber 26 to the source of negative fluid pressure 30, the membrane 10 is moved away from the recessed surface 8 and towards surface 22 and blood is drawn into the pump cavity 12 from the inlet 14.

In order to pump blood through the pump 2 the inlet 14 has an inlet valve (not shown) and the outlet 16 has an outlet valve (not shown) associated therewith. In operation, when the valve 32 is operated to allow fluid to flow into the drive chamber 26 from the source of positive fluid pressure 28 the inlet valve is closed and the outlet valve is open so the blood within the pump cavity 12 exits the outlet 16 via the outlet valve, and when the valve 32 is operated to allow blood to flow out of the drive chamber 26 to the source of negative fluid pressure 30, the inlet valve is open and the outlet valve is closed such that blood is drawn into the pump cavity 12 through the inlet 14 via the open inlet valve.

Referring to FIG. 2 a blood pump 102 according to the present invention is shown comprising a disposable pump cartridge 104 comprising a rigid plastic shell 106 having conical recess 108 covered by a flexible membrane 110. The flexible membrane 110 is attached to a flat upper surface 117 of the rigid shell 106. The upper surface 117 takes the form of an annular surface which surrounds the circular profile of the recess 108. The recess 108 and the flexible membrane 110 form a pump cavity 112 having an inlet 114 and an outlet 116 leading into and out of the cavity respectively. The cartridge 104 abuts a pump driver 118 comprising a platen 120 having a recessed inner surface 122 therein and a fluid port 124. In use the platen 210 sealingly engages with the cartridge 104 such that the inner surface 122 and the flexible membrane 110 form a pump chamber 126. The fluid port 124 is connectable with a source of positive fluid pressure 28 and a source of negative fluid pressure 30 via a valve 32, controlled by a controller 34 to allow fluid to flow into or out of the pump chamber 126. The membrane 110 is operated in a similar way to the prior art device of FIG. 1.

Referring to FIG. 3, the upper surface 117 and inner surface 122 are shown in further detail. The upper surface 117 and inner surface 122 are separated by the transition surface 123 which is curve so as to provide a smooth transition of the membrane 110 between the upper and inner surfaces upon actuation. The effect of this transition surface is to eliminate the dead spot observed between the membrane 10 and the recessed surface 22 of the prior art pump of FIG. 1 as the membrane is able to deflect in a more controlled manner upon actuation. Furthermore the smooth transition of the membrane reduces the stress observed in the membrane 110.

This process is shown in more detail in FIG. 4 which shows the pump chamber membrane 110 (not to scale for illustrative purposes) in a series of position of increasing actuation from 110A to 110F. This illustrates the gradual folding of the membrane over the transition surface 123 and the inner surface 122. This provides increased predictability of the pumped volume for a given stroke position, reduces fluid damage and increases the accuracy of the dispensed volume. Additionally the membrane life is improved by a less severe deflection profile, and in particular reduced stress concentration when compared with the part of the prior art membrane situated at the top of the recessed surface 22 of the prior art.

It will be appreciated that the pump of the present invention could be used to pump extracorporeal blood, water, partly or fully formed dialysate solution, or other suitable medical liquid used in dialysis or similar medical processes requiring the control of fluid.

The invention claimed is:

1. An extracorporeal blood circulation pump comprising:
   a pump cavity that receives and expels extracorporeal blood that is circulated from and to a patient;
   an upper surface peripheral to the pump cavity;
   a transition surface arranged between the upper surface of the extracorporeal blood circulation pump and an inner surface of the pump cavity;
   a deformable membrane that pumps the extracorporeal blood from the pump cavity while the membrane is actuated between a first position and a second position by application of fluid pressure directly to one side of the membrane, the pump cavity being substantially conical such that the membrane is actuated to extend into the pump cavity in order to pump the extracorporeal blood from the pump cavity by touching against the transition surface and the inner surface of the pump cavity to expel the extracorporeal blood between (a) the membrane and (b) the transition surface and the inner surface of the pump cavity;
   the transition surface having a curved profile that, as a consequence of the curved profile not having sharp angles, inhibits the membrane leaving dead spots (a) where, because of a sharp angle, the membrane would fail to touch the transition surface or the inner surface of the pump cavity as the membrane extends into the pump cavity, and (b) where trapped extracorporeal blood would fail to be expelled because it is left behind in a dead spot as the membrane extends into the pump cavity; and
   wherein, as a consequence of the curved profile inhibiting the membrane leaving the dead spots, the curved profile reduces blood damage due to the trapped extracorporeal blood pooling in the dead spots, and increases accuracy of a dispensed volume of the extracorporeal blood actually expelled from the pump cavity, as compared to the blood damage that would occur and the accuracy of the dispensed volume that would be achieved if the transition surface did not have the curved profile inhibiting the membrane from leaving dead spots.

2. The extracorporeal blood circulation pump of claim 1, wherein:
   the pump cavity is frustoconical.

3. A dialysis machine comprising: an extracorporeal blood circulation pump having:
   a pump cavity that receives and expels extracorporeal blood that is circulated from and to a patient:
   an upper surface peripheral to the pump cavity; a transition surface arranged between the upper surface of the extracorporeal blood circulation pump and an inner surface of the pump cavity;
   a deformable membrane that pumps the extracorporeal blood from the pump cavity while the membrane is actuated between a first position and a second position by application of fluid pressure directly to one side of the membrane, the pump cavity being substantially conical such that the membrane is actuated to extend into the pump cavity in order to pump the extracorporeal blood from the pump cavity by touching against the transition surface and the inner surface of the pump cavity to expel the extracorporeal blood between (a) the membrane and (b) the transition surface and the inner surface of the pump cavity;
   the transition surface having a curved profile that, as a consequence of the curved profile not having sharp angles, inhibits the membrane leaving dead spots (a) where, because of a sharp angle, the membrane would fail to touch the transition surface or the inner surface of the pump cavity as the membrane extends into the pump cavity, and (b) where trapped extracorporeal blood would fail to be expelled because it is left behind in a the dead spot as the membrane extends into the pump cavity; and
   wherein, as a consequence of the curved profile inhibiting the membrane leaving the dead spots, the curved profile reduces blood damage due to the trapped extracorporeal blood pooling in the dead spots, and increases accuracy of a dispensed volume of the extracorporeal blood actually expelled from the pump cavity, as compared to the blood damage that would occur and the accuracy of the dispensed volume that would be achieved if the transition surface did not have the curved profile inhibiting the membrane from leaving dead spots.

4. The dialysis machine of claim 3, wherein:
the pump cavity is frustoconical.

\* \* \* \* \*